United States Patent [19]

Sahota

[11] Patent Number: 5,143,093
[45] Date of Patent: Sep. 1, 1992

[54] METHODS OF ANGIOPLASTY TREATMENT OF STENOTIC REGIONS

[76] Inventor: Harvinder Sahota, 3861 Wisteria, Seal Beach, Calif. 90740

[21] Appl. No.: 593,666

[22] Filed: Oct. 5, 1990

[51] Int. Cl.$^5$ ............................................ A61M 29/02
[52] U.S. Cl. .................................. 128/898; 606/194; 604/96
[58] Field of Search .................... 606/194, 192, 196; 604/96; 128/898

[56] References Cited

U.S. PATENT DOCUMENTS

| | | |
|---|---|---|
| 2,930,377 | 3/1960 | Cowley . |
| 3,045,677 | 7/1962 | Wallace . |
| 3,448,739 | 6/1969 | Stark et al. . |
| 3,889,686 | 6/1975 | Duturbure . |
| 4,029,104 | 6/1977 | Kerber ............... 128/656 X |
| 4,040,413 | 8/1977 | Ohshiro . |
| 4,233,983 | 11/1980 | Rocco . |
| 4,329,993 | 5/1982 | Lieber et al. . |
| 4,338,930 | 7/1982 | Williams . |
| 4,423,725 | 1/1984 | Baran et al. . |
| 4,461,280 | 7/1984 | Baumgartner . |
| 4,527,549 | 7/1985 | Gabbay . |
| 4,546,759 | 10/1985 | Solar . |
| 4,547,193 | 10/1985 | Rydell . |
| 4,563,181 | 1/1986 | Wijayarathna et al. . |
| 4,564,014 | 1/1986 | Fogarty et al. ............... 606/194 |
| 4,581,017 | 4/1986 | Sahota . |
| 4,644,936 | 2/1987 | Schiff . |
| 4,689,040 | 8/1987 | Thompson . |
| 4,738,666 | 4/1988 | Fuqua . |
| 4,762,129 | 8/1988 | Bonzel . |
| 4,763,654 | 8/1988 | Jang . |
| 4,784,639 | 11/1988 | Patel . |
| 4,822,345 | 4/1989 | Danforth . |
| 4,826,480 | 5/1989 | Diaz et al. . |
| 4,950,239 | 8/1990 | Gahara et al. ............... 604/96 |
| 4,976,690 | 12/1990 | Solar et al. ............... 604/96 |
| 5,000,743 | 3/1991 | Patel ............... 606/194 |

FOREIGN PATENT DOCUMENTS

| | | |
|---|---|---|
| 0214721 | 3/1987 | European Pat. Off. . |
| 8303766 | 11/1983 | World Int. Prop. O. . |

OTHER PUBLICATIONS

Spencer B. King et al., *Coronary Arteriography and Angioplasty*, McGraw-Hill Book Company, pp. 399–460.
John B. Simpson et al., "A New Catheter System for Coronary Angioplasty", The American Journal of Cardiology, vol. 49, Apr. 1, 1982, pp. 1216–1222.
Martial G. Bourassa, M.D., *Bourassa Cardiovascular Catheters Sterile*, USCI 1972, 604/281.
Gerald Dorros, M.D. et al., *Probe ™, A Balloon Wire: Initial Experience, Catheterization and Cardiovascular Diagnosis*, vol. 14, 1988, pp. 286–288.
Steerable Balloon Dilatation System, ©C.R. Bard, Inc. 1982.
Abstract of WO89/03701, Harmjanz, D. May 5, 1989.
USCI Gruntzig ™ Femoral, Iliac and Gruntzig Dilaca ™ Renal Dilatation Catheters, C.R. Bard, Inc. 1980.
Safety Spring Guides, ©C.R. Bard, Inc. 1979.
Gruntzig Dilaca ® Coronary Balloon Dilatation Catheters, ©C.R. Bard, Inc. 1982 USCI ® Probing Catheter.
USCI Positrol II ® & Nycore ™ Cardiovascular Catheters, ©C.R. Bard, Inc. 1980.
USCI Gruntzig Dilaca ™ Coronary Dilatation Equipment, ©C.R. Bard, Inc. 1982.
USCI ® Gruntzig Dilaca ™ Coronary Dilatation Equipment, ©C.R. Bard, Inc. 1981.
The Simpson-Robert ™ Vascular Dilation System for Percutaneous Transluminal Coronary Angioplasty (PTCA), Advanced Catheter Systems, Inc.
Cordis Infusion Catheter Set, A Simple, Reliable System for Thrombolysis of Coronary and Other Arteries, ©Cordis Corporation 1982.
"Balloon Dilatation for Congenital Pulmonary Valve Stenosis", Cardiology Product News/Jan. 1983.

*Primary Examiner*—Michael H. Thaler
*Attorney, Agent, or Firm*—Knobbe, Martens, Olson & Bear

[57] ABSTRACT

Dilation catheters for use in administering treatments to relieve stenotic regions within a body lumen are described. In the invention, a novel catheter system having a balloon length of minimal length for treating distal arteries is utilized. In addition, novel methods for treating stenotic areas which are present in tortuous vessels, as well as hardened, or calcified stenotic portions are also described.

2 Claims, 3 Drawing Sheets

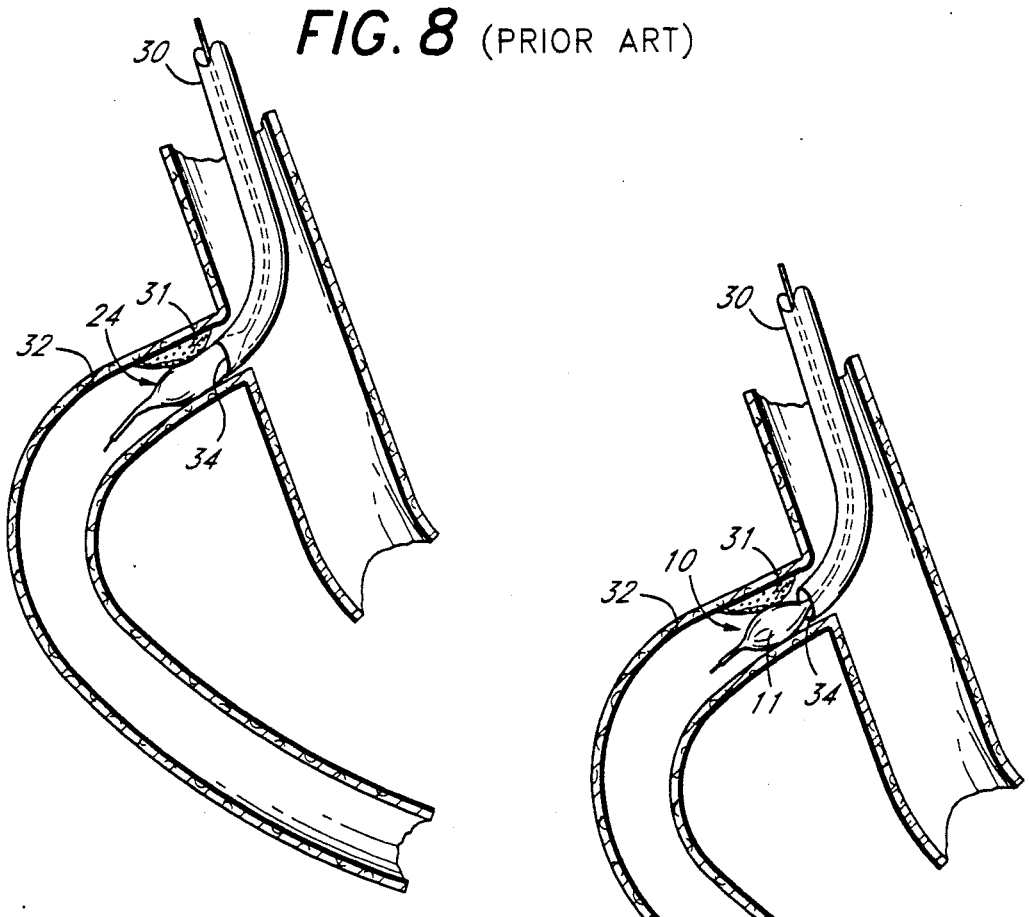
FIG. 8 (PRIOR ART)
FIG. 9
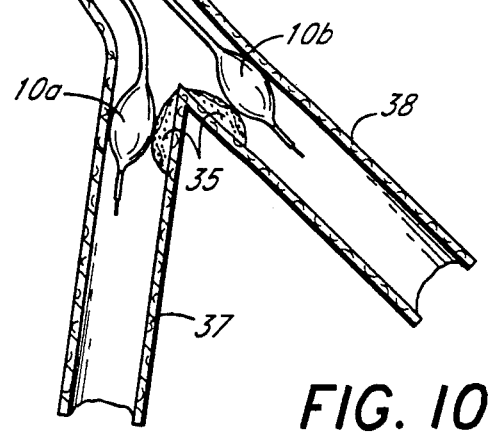
FIG. 10

METHODS OF ANGIOPLASTY TREATMENT OF STENOTIC REGIONS

BACKGROUND OF THE INVENTION

The present invention relates generally to the field of catheters. More specifically, the present invention relates to dilation catheters for use in administering treatments to relieve a stenotic region or to widen a constricted blood flow or tubular passage, such as the coronary artery, as well as other vessels.

Percutaneous transluminal coronary angioplasty (PTCA), a procedure for treating a patient having a stenosis or constricted blood region in a coronary artery, has become a widely accepted therapeutic alternative to coronary arterial bypass surgery for many patients. PTCA increases the lumen by radial expansion. The main advantage of the PTCA procedure is in reducing morbidity and avoiding the immediate postoperative discomforts associated with coronary bypass surgery.

However, the benefits of PTCA are restricted to those lesions accessible to the balloon dilation catheter. With standard balloon systems, certain lesions are inaccessible due to variations in the patient's anatomy and vasculature. Further, seducing side branches, tortuous vessels, and the more distal arteries have presented serious difficulties in the PTCA procedure because, due to its length, the balloon could not reach the stenotic region.

When considering angioplasty as a method of treating stenotic regions, the morphology of the lesion is critical in determining whether the vessel will adequately dilate. If the stenosis is comprised primarily of fatty deposits, for example, it is possible to compress the stenosis radially outwardly, against the adjacent vessel wall, so as to increase the cross-sectional area of the vessel, and provide adequate perfusion through the vessel. If, however, the artery is hard, or the stenosis has calcified, the artery may be dissected if inflated with a standard dilation balloon.

Performing a coronary angioplasty involves the difficulty of inserting a balloon catheter into the desired coronary artery. Most balloon catheters are too flexible for direct insertion into the patient's coronary artery. Accordingly, the standard angioplasty process begins with the insertion of a guide wire into the obstructed vessel, under local anesthesia. A guiding catheter, or sleeve is then slipped over the wire. The guiding catheter is designed to provide a conduit through which a balloon catheter is passed. The tip of the guiding catheter is not tapered so as to permit the unimpeded passage of the balloon catheter therethrough.

The lesion may be approached with a guide wire by advancing the catheter and guide wire as a unit, or by advancing the guide wire first. Steering the tip of the wire is done by the surgeon or by an assistant. If the tip is moving in an undesired direction, then slightly withdrawing and torquing the guide wire will rotate the tip toward in desired direction. Once the wire is positioned, the balloon catheter may be advanced over the wire until it crosses the lesion. The balloon advances until it reaches the tip, which the surgeon has maintained in a fixed position in the distal artery. The cardiologist positions the balloon in the artery, expands the balloon, and then allows the balloon to depressurize to permit measurement of blood flow across the stenosis.

The benefits of angioplasty are restricted to lesions accessible to the balloon dilation catheter. With currently available balloon systems, (2 mm or longer in length) certain lesions are inaccessible due to variations in the patient's anatomy and vasculature. Further, seducing side branches, tortuous vessels, and the more distal arteries have presented serious difficulties in the PTCA procedure because, due to its length, the balloon can not effectively seduce these stenotic regions.

These difficult areas include, (1) the area immediately after the left main artery, in which there is a narrowing of the left anterior descending artery (LAD), (2) those areas of the heart where acute angled branching occurs along a bend in the artery, (3) lesions near the origin of the aortic artery and (4) bifurcation lesions. These special and difficult situations cannot adequately be treated with long catheters. Seducing such tortuous vessels is quite difficult using the standard, longer dilation balloons.

SUMMARY OF THE INVENTION

The dilation catheters of the present invention overcome many of the difficulties associated with ordinary prior art dilation catheters. The short length of this balloon lends itself to easy maneuverability, both during insertion and inflation. The short balloon directly attached on a wire increases its accessibility to distil narrowings. In some arteries, for example, the left anterior descending artery, there are many sharp bends and curves. Seducing such tortuous vessels can prove quite difficult using standard length dilation balloons. The short dilation balloon of the present invention advantageously are easier to manipulate through the arteries, both during insertion and inflation thereof. Thus, acute bends or branches may be crossed or dilated easier, quicker, with less trauma to the artery and with a substantial reduction in the risk of dissection.

In addition, the short balloon does not impede the flow of blood in the left main artery while dilating a lesion in LAD. A reduction of blood flow in this artery even temporarily is very damaging to the heart.

Further, when seducing a right coronary artery lesion, the longer balloon extends over the guide catheter which prevents inflation. Thus the surgeon must remove the guide during inflation and insert it back into the artery after deflation. This repetitive maneuver increases the risk of trauma to the ostium. The shorter balloon eliminates this risk since it is completely out of the guide and in the right coronary artery.

The shorter balloon is also advantageous in seducing bifurcation lesions. This procedure requires the insertion of two balloons simultaneously. Two short balloons are easier to manipulate, maneuver, and place during this procedure than the long balloon. Again, a longer balloon is more likely to obstruct the proximal part of the artery before the bifurcation.

The present long balloons can not perform all of these functions. The outcome of their inherit design limitations are unsuccessful angioplasties resulting in patients requiring open heart surgery.

Further objects, features and other advantages of the present invention will become apparent from the ensuing detailed description, when considered together with the appended drawings.

BRIEF DESCRIPTION OF THE DRAWINGS

FIG. 8 is a partial cross-sectional view illustrating a prior art dilation balloon positioned within a right coronary artery lesion;

FIG. 9 is a partial cross-sectioned view illustrating the dilation balloon of FIGS. 1-4 positioned within a right coronary artery lesion; and FIG. 10 is a partial cross-sectional view of two short dilation catheters of FIGS. 1-4 positioned within a branching artery containing a bifurcation lesion.

DETAILED DESCRIPTION OF THE PREFERRED EMBODIMENT

Figure 1:
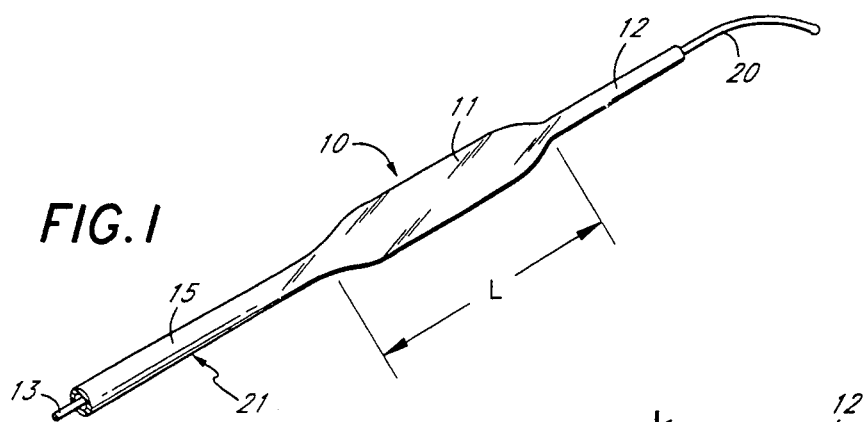
FIG. 1 is a perspective view of a short dilation catheter having a materially shortened length L constructed in accordance with the present invention.
Figure 2:
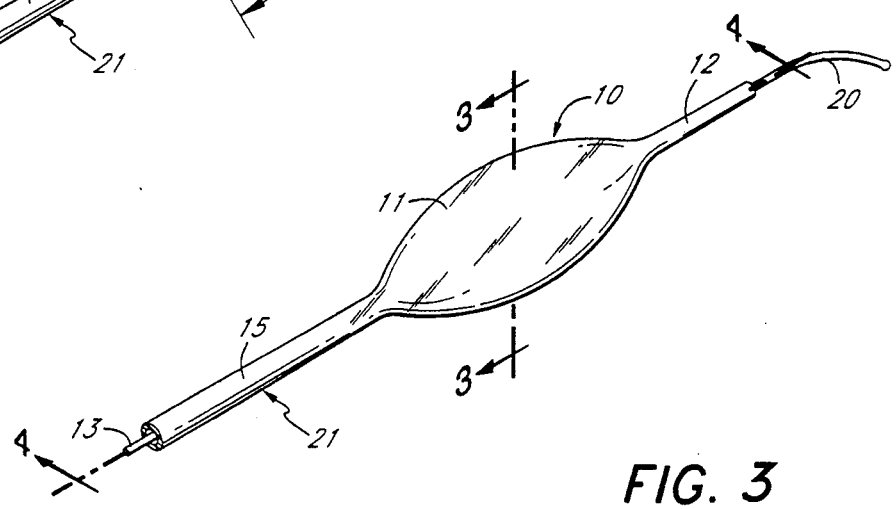
FIG. 2 is a perspective view of the short dilation catheter showing the dilation balloon in its inflated state.
Figure 3:
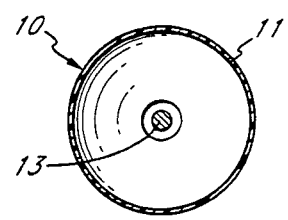
FIG. 3 is a cross-sectional view, taken along line 3—3 of FIG. 2.
Figure 4:
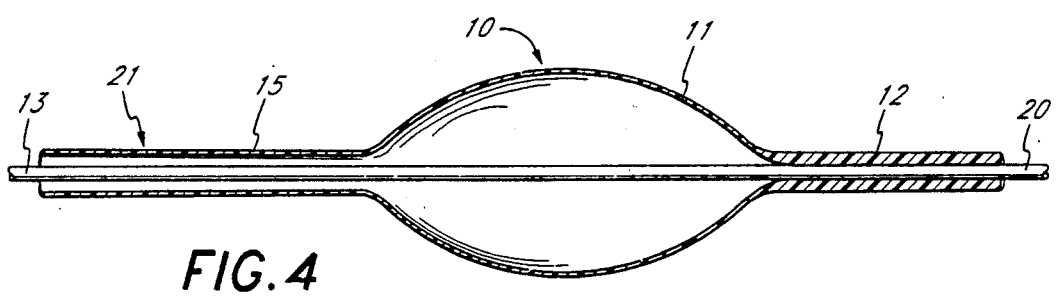
FIG. 4 is a cross-sectional view, taken along line 4—4 of FIG. 2, illustrating the short dilation balloon.

Referring now to the drawings in detail, wherein like reference numerals designate like elements throughout the several views thereof, there is shown generally at 10, in FIGS. 1-4, a dilation catheter embodying the present invention in a preferred form. The catheter 10 comprises a dilation balloon 11, having a distal end 12 which is fastened around an axially elongate guide wire 13. By attaching the dilation balloon 11 directly on the wire 13, the catheter 10 is especially adapted for insertion into the most distal arteries which are much narrower than the main coronary artery.

Advantageously, the dilation balloon 10 is attached to the wire 13 only at the distal end 12, leaving the wire 13 free to move within the catheter shaft 15. Preferably, the wire 13 extends the length of the catheter 10, and exhibits a small segment, referred to as an advance wire 20, which extends beyond the distal end 12 of the dilation balloon 10. The advance wire 20 may be of any suitable length, and may be preformed to any desired configuration to facilitate insertion of the catheter 10 and passage through the body lumen.

The proximal end 21 of the dilation balloon 10 tapers to a diameter which approaches that of the wire 13 to form the shaft 15 of the catheter 10. Thus, the catheter shaft 15 is an extension of the dilation balloon 11. The catheter shaft 15 provides a path for conducting pressurized fluids into and out of the balloon 11 for selective expansion and deflation thereof. Preferably, the balloon 11 and shaft 15 of the catheter 10 are made of a non-distensible material so that it can only be inflated to expand to the constructed size. Further attempts to inflate such structures result in an increase in pressure, but no significant increase in diameter.

The dilation catheter 10 illustrated in FIGS. 1-4 is particularly suited for performing methods of angioplasty treatment of stenotic regions of distal arteries. The balloon 11 of the present invention is materially shorter than conventional prior art angioplasty balloons. Such prior art catheters have a balloon length of two millimeters or more. In contrast, the balloon 11 of the present invention is considerably shorter with a length L preferably in the range of one-half (0.5) millimeter to one (1.0) millimeter.

The angioplasty procedures of the invention are performed by surgeons employing catheters constructed in accordance with FIGS. 1-4. As noted above, these catheters advantageously have balloon lengths L of approximately 0.5 millimeter and 1.0 millimeter. In addition, benefits of the invention in certain angioplasty procedures will accrue using a catheter having a balloon length L of between 1.0 and 1.5 millimeter.

In use, the catheter 10 is inserted into the body lumen until the dilation balloon 11 is proximate the stenotic area. Following several inflations and deflations, the balloon 11 is withdrawn across the lesion. The catheter 10 is left in place in the body lumen for a short period of time, referred to as the post-dilation observation period, to ensure that the lumen will not collapse. If re-occlusion does occur, then the same balloon catheter 10, or a different balloon catheter (not shown), can be passed across the lesion and the vessel redilated. This is particularly significant in dealing with the more distal arteries, to which access is often times difficult.

The short balloon catheter 10 is extremely useful in negotiating the numerous areas of the heart where there are many acute angles in tortuous vessels and is particularly useful when dilating these same vessels. The short balloon 11 readily expands to dilate stenotic areas, but is of such a length so as not to impede blood perfusion in the proximal arterial branches while the lumen is being dilated. The catheter shaft 15 may be straight, or it may be preformed with different shapes and configurations to facilitate insertion through the body lumen.

Figure 5:
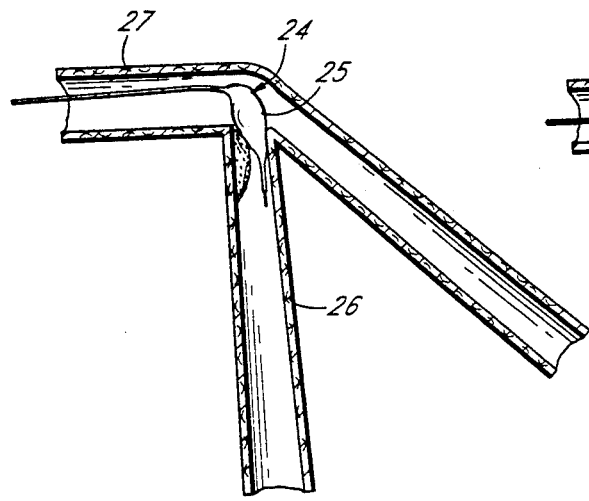
FIG. 5 is a partial cross-sectioned view illustrating the blocking of the left main artery which commonly occurs during prior art angioplasty procedures in the left main artery.

FIG. 5 illustrates a prior art catheter 24. As noted above, this prior art catheter 24 has a balloon 25 whose length is at least 2 millimeters long. As shown in FIG. 5, the prior art balloon 25 is shown inflated to dilate a stenotic area of the left anterior descending artery 26 immediately adjacent the left main artery 27. As shown, because of its length, the prior art balloon 25 blocks a portion of the left main artery 27. Reducing the blood flow in this artery, even temporarily, will damage the heart.

Figure 6:
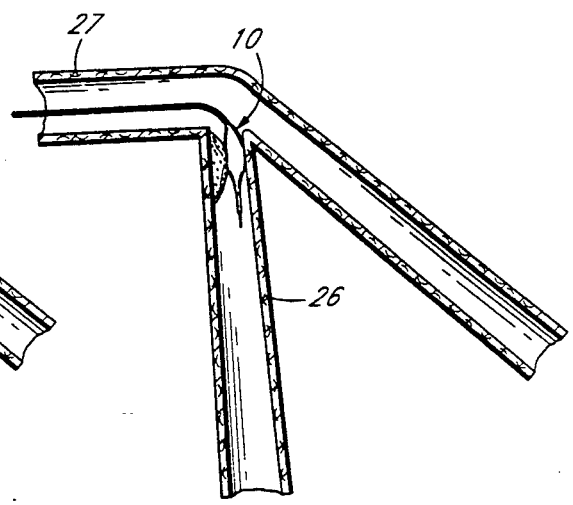
FIG. 6 is a partial cross-sectional view illustrating the dilation balloon of FIGS. 1-4 positioned within a patient's left main artery with the balloon inflated illustrating that the perfusion of blood is not impeded.

FIG. 6 illustrates the short balloon catheter 10 of the invention in an inflated state, within the same left anterior descending artery 26. Significantly, as illustrated, the short balloon catheter 10 of the invention does not obstruct the proximal part of the left main artery, and thus it does not impede the flow of blood in this artery.

Figure 7:
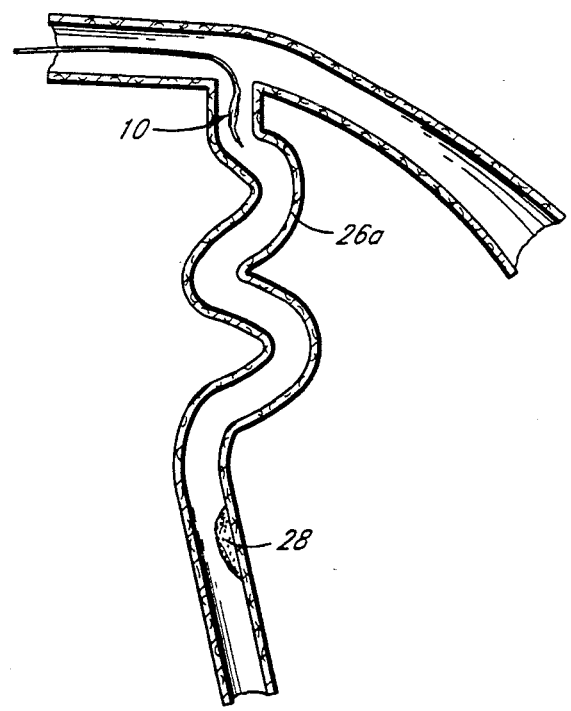
FIG. 7 is a partial cross-sectional view of a dilation catheter within a patient's artery near the heart where acute angled branching occurs along a bend in the artery.

FIG. 7 further illustrates the left anterior descending artery 26a which contains many sharp bends and curves before the catheter can reach a lesion shown at 28. Seducing such tortuous vessels 26a can prove quite difficult using prior art length dilation balloons. The short dilation balloon catheter 10 is very advantageous since it is more maneuverable and easier to manipulate through a tortuous artery 26a, both during insertion and inflation. Thus, the acute bends or branches of artery 26a are crossed or dilated easier, quicker, with less trauma to the artery and with a substantial reduction in the risk of dissection. Also, the short balloon catheter 10 does not force the artery 26a to straighten as the balloon is inflated, thus reducing the risk of dissection of the artery.

Angioplasty treatment methods of a stenotic region of the right coronary artery is illustrated in FIGS. 8 and 9. As shown in FIG. 8, if the guide catheter 30 remains in place, the balloon of prior art catheter 24 will partly remain in the sheath or guide catheter 30, during inflation of a stenosis 31 of the right coronary artery 32 proximal to the ostium of the right coronary artery. As a result, in the prior art method, the surgeon must first pull the distal end 34 of the guide catheter 30 out of the ostium of the right coronary artery 32 before inflation of the prior art catheter balloon catheter 24 and put it back into the artery after deflation. This maneuver can cause trauma to the ostium of the right coronary artery. In contrast, as shown in FIG. 9, in the treatment method of this invention, the balloon 11 of the short catheter 10 is completely out of the guide catheter 30. As a result, the guide catheter 30 need not be removed from the right coronary artery during inflation of the short balloon catheter 10.

Another improved method of performing angioplastic treatment according to the present invention is illustrated in FIG. 10. This Figure illustrates a bifurcation lesion 35. During this procedure, the surgeon simultaneously inserts two balloon catheters. In the prior art (not shown) the prior art balloon catheter with its balloon length of 2 millimeters or longer tends to obstruct the proximal portion 36 of the artery before the bifurcation into the two arteries 37 and 38. In contrast, two short balloon catheters 10a and 10b constructed in accordance with FIGS. 1-4 do not, as shown in FIG. 10, obstruct the artery 36. Moreover, the shorter balloon catheters 10a and 10b will be easier for the surgeon to manipulate and position than the prior art balloon catheters.

It will be appreciated that certain structural variations may suggest themselves to those skilled in the art. The foregoing detailed description is to be clearly understood as given by way of illustration, the spirit and scope of this invention being limited solely by the appended claims.

What is claimed is:

1. A method of negotiating tortuous vessels within the body, and dilating stenotic regions, including hardened, calcified stenotic portions in the left anterior descending artery, without obstructing the blood flow in the downstream branch of the left main artery, comprising the steps of:

inserting an axially elongate dilation catheter having a dilation balloon between 0.5 millimeter and 1.0 millimeter in length into said left anterior descending artery, so as to (i) position said dilatation balloon adjacent said stenosis, said stenosis being located in the left anterior descending artery at the intersection with the left main artery and (ii) position substantially the entire dilation balloon out of said branch of left main artery;

injecting a pressurized fluid into said dilation balloon so as to increase the size of said balloon by radial expansion without obstructing the blood flow in the portion of the left main artery which is downstream from the intersection with the left anterior descending artery; and deflating said dilation balloon.

2. A method of angioplastic treatment of a stenotic region of the right coronary artery in which the guide catheter remains in place in the right coronary artery even though the stenosis is proximate to the ostium of the right coronary artery, comprising the steps of:

inserting the distal end of a sheath guide catheter into said ostium;

passing a balloon catheter through said sheath guide catheter until the balloon is entirely out of said sheath guide catheter and is in juxtaposition with said stenosis, said balloon catheter having a balloon length of about 0.5 millimeter so that the proximal end of the balloon is disposed anatomically distally of the ostium;

injecting a fluid into said balloon to inflate said balloon and to increase the diameter of said balloon and decrease the size of said stenosis while the distal end of said sheath guide catheter remains within said ostium;

removing said fluid from said balloon to deflate same; and withdrawing said balloon catheter through said sheath guide catheter and withdrawing, for the first time, said sheath guide catheter from said ostium.

* * * * *